(12) United States Patent
Bowen, Jr. et al.

(10) Patent No.: US 6,833,362 B2
(45) Date of Patent: Dec. 21, 2004

(54) METHOD AND COMPOSITION FOR THE ACCELERATED IN VIVO REMOVAL OF ETHANOL

(76) Inventors: Ward Beryl Bowen, Jr., 8107 Ridge Rd. West, Brockport, NY (US) 14420-1732; Daniel Salman Daniel, 3051 St. Paul Blvd., Rochester, NY (US) 14617

( * ) Notice: Subject to any disclaimer, the term of this patent is extended or adjusted under 35 U.S.C. 154(b) by 66 days.

(21) Appl. No.: 09/876,322

(22) Filed: Jun. 7, 2001

(65) Prior Publication Data

US 2002/0015741 A1 Feb. 7, 2002

Related U.S. Application Data

(60) Provisional application No. 60/210,950, filed on Jun. 12, 2000.

(51) Int. Cl.$^7$ .................... A61K 31/07; A61K 31/28; A61K 31/295; A61K 31/30; A61K 31/315; A61K 31/32; A61K 31/60; A61K 31/609; A61K 31/7076; A61K 33/00; A61K 33/24; A61K 33/26; A61K 33/30; A61K 33/32; A61K 33/34

(52) U.S. Cl. .................. 514/47; 424/94.3; 424/94.4; 424/449; 424/451; 424/600; 424/604; 424/606; 424/617; 424/618; 424/626; 424/630; 424/638; 424/639; 424/641; 424/642; 424/643; 424/644; 424/646; 424/649; 424/650; 424/654; 424/655; 424/715; 424/716; 424/717; 424/725; 424/754; 514/23; 514/24; 514/25; 514/26; 514/27; 514/28; 514/32; 514/33; 514/35; 514/45; 514/46; 514/48; 514/49; 514/50; 514/51; 514/52; 514/53; 514/54; 514/62; 514/161; 514/162; 514/163; 514/164; 514/165; 514/166; 514/184; 514/185; 514/188; 514/189; 514/190; 514/251; 514/276; 514/345; 514/351; 514/412; 514/451; 514/453; 514/456; 514/457; 514/458; 514/460; 514/464; 514/474; 514/492; 514/493; 514/494; 514/495; 514/496; 514/498; 514/499; 514/500; 514/501; 514/502; 514/505; 514/556; 514/561; 514/562; 514/563; 514/564; 514/565; 514/570; 514/617; 514/669; 514/693; 514/698; 514/937; 514/958; 514/962; 426/74; 426/615; 426/648

(58) Field of Search ............... 424/94.3, 94.4, 424/449, 451, 600, 604, 606, 617, 618, 626, 630, 638, 639, 641–644, 646, 649, 650, 654, 655, 715–717, 725, 754; 514/23–28, 32, 33, 35, 45–54, 62, 161–166, 184–185, 188–190, 251, 276, 345, 351, 412, 451, 453, 456–458, 460, 464, 474, 492–496, 498–502, 505, 556, 561–565, 570, 617, 669, 693, 698, 937, 958, 962; 426/74, 615, 648

(56) References Cited

U.S. PATENT DOCUMENTS 5,053,396 A * 10/1991 Blass ................ 514/45

FOREIGN PATENT DOCUMENTS

WO 98/20332 * 5/1998

OTHER PUBLICATIONS

Crans, Debbie C. et al., "Chemically induced modification of cofactor specificity of glucose–6–phosphate dehydrogenase," Journal of the American Chemical Society, vol. 114 (12), Jun. 1992, pp. 4926–4928.*

* cited by examiner

*Primary Examiner*—John Pak
(74) *Attorney, Agent, or Firm*—Brian B. Shaw, Esq.; Donna P. Suchy, Esq.; Harter, Secrest & Emery LLP

(57) ABSTRACT

A composition for accelerating the disposal of ethanol from bodily fluid. Certain additives can accelerate the metabolic oxidation of ethanol, and others in addition act as catalysts or "pseudo" enzymes for the oxidation. Additives include the oxidant Nicotinamide Adenine Dinucleotide and a variety of other additives such as transition metal ions and complexes thereof which favor the oxidation reaction. The compositions described can act as a sobriety inducer and/or as an effective palliative for the unpleasant effects of overuse of ethanol.

63 Claims, 2 Drawing Sheets

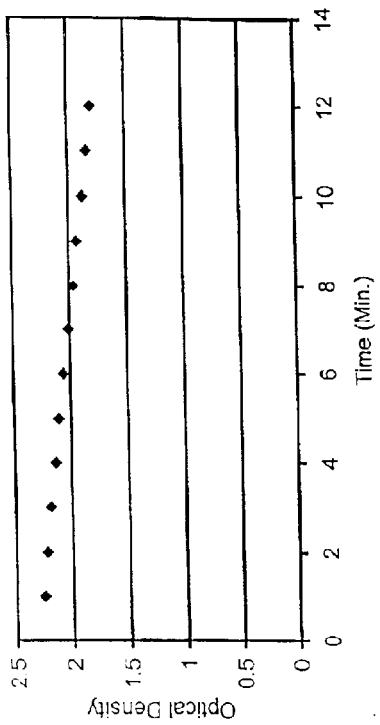
Fig. 1a: Oxidation of NADH by VOSO4 at pH 9.25
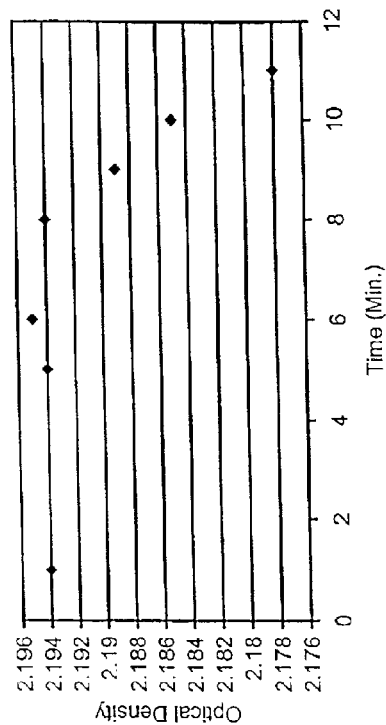
Fig. 1c: Oxidation of NADH by potassium ferricyanide at pH 9.25
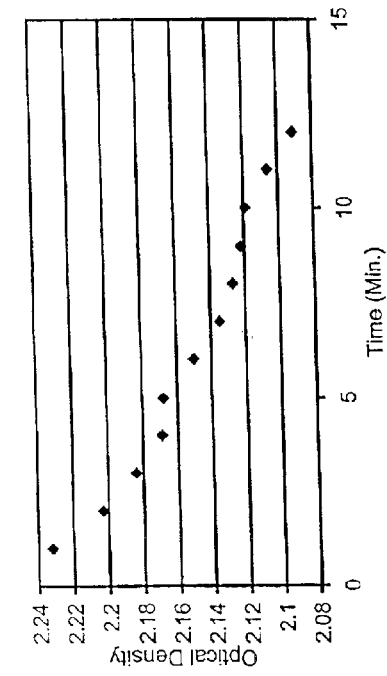
Fig. 1b: Oxidation of NADH by sodium phosphotungstate at pH 9.25
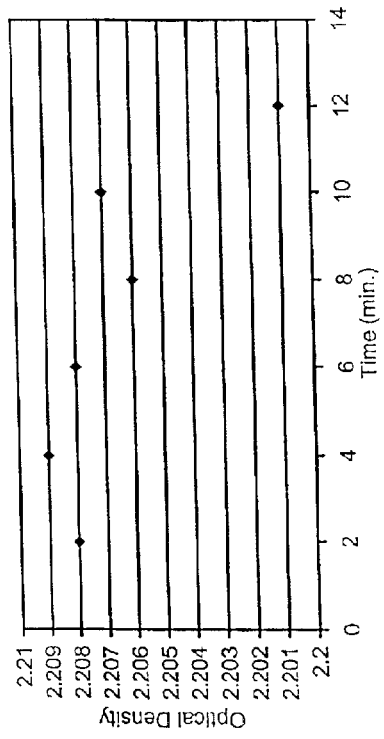
Fig. 1d: Oxidation of NADH by ammonium molybdate at pH 9.25

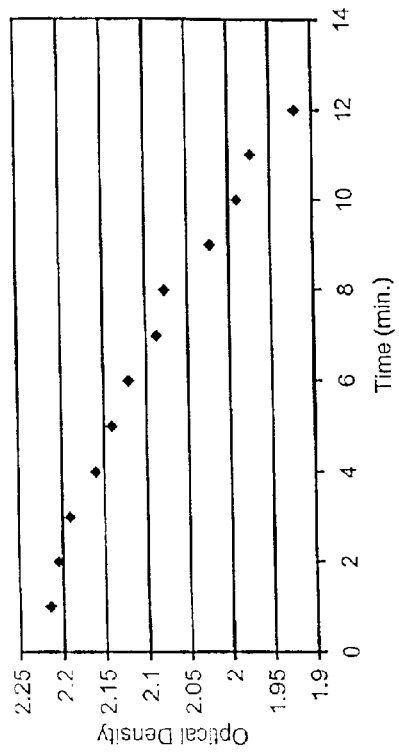
Fig. 2a: Oxidation of NADH by VOSO4 at pH 7.25
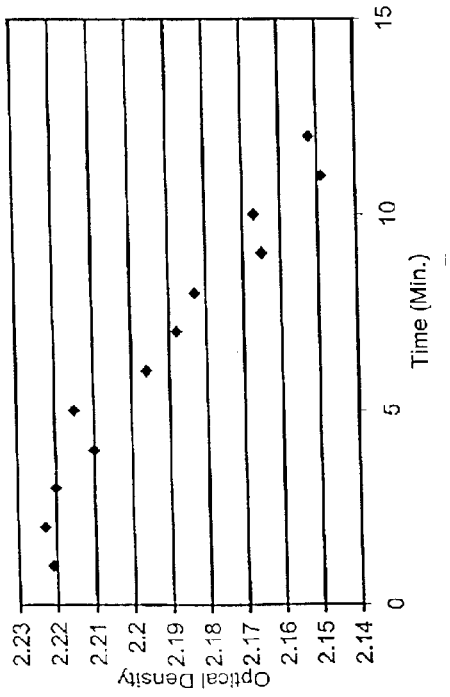
Fig. 2b: Oxidation of NADH by sodium phosphotungstate at pH 7.25
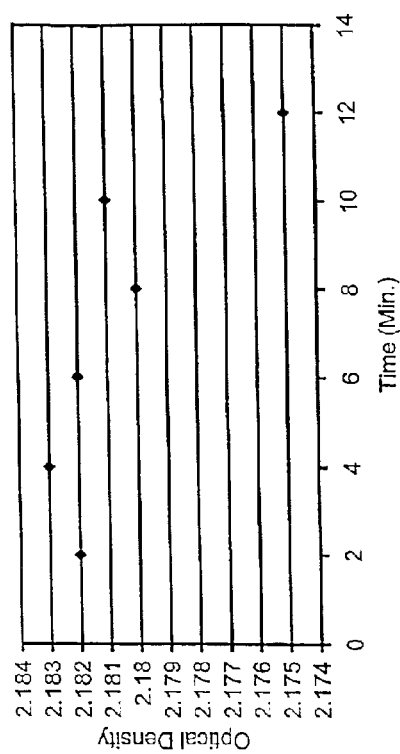
Fig. 2c: Oxidation of NADH with potassium ferricyanide at pH 7.25
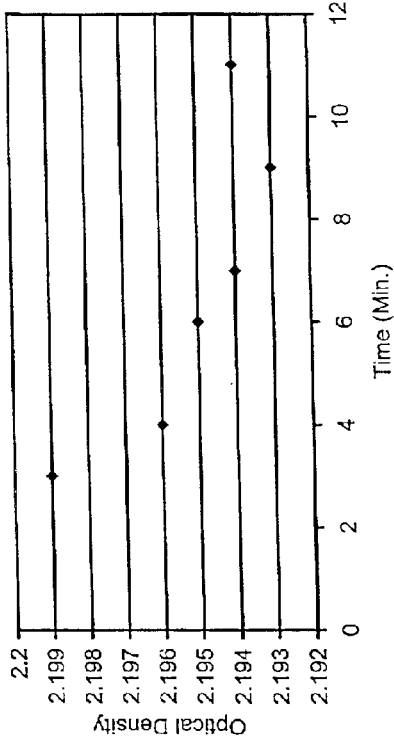
Fig. 2d: Oxidation of NADH by ammonium molybdate at pH 7.25

METHOD AND COMPOSITION FOR THE ACCELERATED IN VIVO REMOVAL OF ETHANOL

This application claims the benefit of Provisional application Ser. No. 60/210,950, filed on Jun. 12, 2000.

FIELD OF THE INVENTION

This invention relates to compositions and processes which accelerate the oxidation of alcohol in human blood. More particularly, the invention provides for the enhanced in vivo oxidation of ethanol and/or methanol.

BACKGROUND OF THE INVENTION

Alcohol consumption and its consequences have long been a challenge to the statutes that govern our society. High levels of ethanol in the blood have far reaching consequences to the user and society, as indicated by 16000 highway deaths and 1.6 million drinking related arrests per year in the United States.

Therefore there is a need to provide a remedy which can be administered to accelerate removal of alcohol from an individual's bloodstream and therefore to shorten the period during which the individual is impaired.

There is also a need to provide a remedy to an individual who is affected by alcohol to such a degree that medical intervention is required.

The source of oxygen, both mechanical and chemical (including the use of catalase in combination with hydrogen peroxide) is an essential part of the process, both these enzymes are NOT oxygen dependent but rather use $NAD^+$ as the oxidizing agent.

Even though the combination can include other enzymes, which regenerate NADH to $NAD^+$, using glycerol dehydrogenase/dihydroxyacetone, the presence of a liberal supply of oxygen is an essential part of the method.

SUMMARY OF THE INVENTION

Formally, the oxidation of ethanol to acetaldehyde and then to acetic acid can be generically represented by the reactions:

$$C_2H_5OH + 2H_2O \leftrightarrows CH_3CHO + 2H_3O^- + 2e \quad (1)$$

$$CH_3CHO + 4H_2O \leftrightarrows CH_3CO_2^- + 3H_3O^+ + 2e \quad (2)$$

It is therefore the object of this invention to accelerate the rates of the forward reactions in the equilibria 1 and 2, by introducing additives which catalyze the forward reactions or which remove product from the right hand side of the equilibria 1 and 2 to favor their shifting to the right.

Various additives provide a remedy through an effective and rapid reduction of the alcohol level in blood of the consumer at a reasonably short time, in essence a sobriety agent. Such remedy can take the form of a liquid, a pill, a capsule, a patch or a nasal spray or any other method known to medical science and any combination thereof. Such remedy can be self-administered or, in the same or different formulation be administered at a health care facility where it can be applied intravenously, intraperitoneally or in any other method known in medical practice. The product shall apply to all alcohol containing beverages including but not limited to all beers, wines and hard liquors now in use.

BRIEF DESCRIPTION OF THE DRAWINGS

FIG. 1a is a graph of the oxidation of NADH by vanadyl sulfate at pH 9.25.

FIG. 1b is a graph of the oxidation of NADH by sodium phosphotungstate at pH 9.25.

FIG. 1c is a graph of the oxidation of NADH by potassium ferricyanide at pH 9.25.

FIG. 1d is a graph of the oxidation of NADH by ammonium molybdate at pH 9.25.

FIG. 2a is a graph of the oxidation of NADH by vanadyl sulfate at pH 7.25.

FIG. 2b is a graph of the oxidation of NADH by sodium phosphotungstate at pH 7.25.

FIG. 2c is a graph of the oxidation of NADH by potassium ferricyanide at pH 7.25.

FIG. 2d is a graph of the oxidation of NADH by ammonium molybdate at pH 9.25.

DETAILED DESCRIPTION OF THE PREFERRED EMBODIMENTS

The present invention relates to compositions which when administered to a person enhance the in vivo physiological process of removing oxidizing alcohol and particularly from the blood. In this disclosure, the term "alcohol" when used without qualification is understood to refer to ethanol. However, certain embodiments of the invention as noted will also be applicable to methanol.

As alcohol enters the blood stream, the liver begins the process of detoxification through the production of the enzyme Alcohol Dehydrogenase, ADH, which catalyzes the oxidation by Nicotinamide Adenine Dinucleotide, $NAD^+$, of ethanol to acetaldehyde and Dihydronicotinamide Adenine Dinucleotide, NADH, as shown.

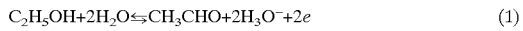
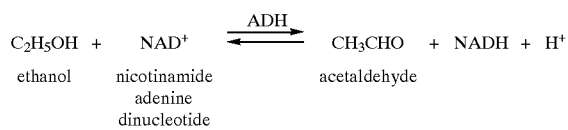

The equilibrium constant of this reaction is 1, indicating that it is rather inefficient, allowing sufficient amounts of alcohol to remain in the blood and to cross the blood-brain barrier. It is the purpose of this invention to find ways of increasing the efficacy or accelerating this reaction.

In one embodiment of this invention, accelerated oxidation is accomplished by introducing a chemical accelerator of the ADH enzyme, driving the reaction toward acetaldehyde. Such accelerators include zinc ions (as ADH is a Zinc Enzyme), pyridoxamine or pyridoxamine phosphate (formulae 1a and 1b) or a combination thereof.

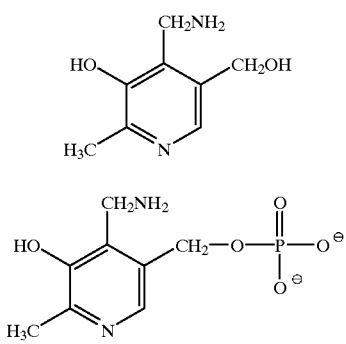

It is a particular advantage in the case of one of the above accelerators (zinc) that it is an essential element or a part of the Vitamin B6 system (pyridoxamine).

In another embodiment of this invention, the reversible reaction above can be shifted toward irreversibility by the removal of one or more of the products (Le Chatelier's Principle). This is accomplished through the introduction of a reactive agent that by reacting with acetaldehyde (removing it from the equilibrium) drives the reaction forward. Such an agent includes pyridoxamine or pyridoxamine phosphate (formulae 1a and 1b) or the basic amino acids lysine (formula 2) and arginine (formula 3). A solubilized form of "Purpald" (formula 4) may also be useful. Other agents reactive with acetaldehyde include thiamine. A sufficient quantity of the reactive agent is administered to provide an in vivo concentration of the reactive agent at least chemically equivalent to an amount of acetaldehyde resulting from the oxidation.

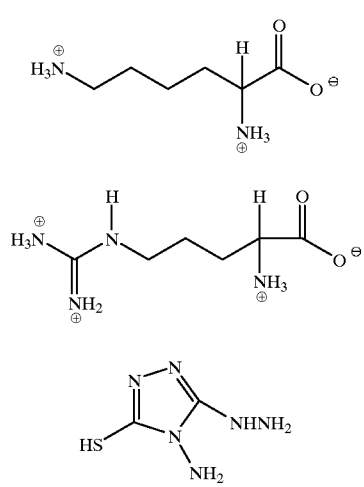

Lysine and arginine being essential amino acids, their introduction would not cause an undue risk to the user. Further, being basic, these amino acids can help neutralize the acid formed during the oxidation, thus further shifting the equilibrium toward product.

In the presence of a base, the acetic acid produced by equilibrium (2) is neutralized, which pulls the reaction to the right. This consumes acetaldehyde from equilibrium (1), which is thus pulled to the right and consumes more ethanol.

Any base can be used provided that it is not harmful to the body. For example, the base can be sodium carbonate, sodium bicarbonate, trisodium phosphate, disodium hydrogen phosphate or tris(hydroxymethyl)-aminomethane. A sufficient quantity of the base is administered to provide an in vivo concentration of the base at least chemically equivalent to the acid resulting from the oxidation of the ethanol.

The removal of acetaldehyde can also be accomplished by its enzymatic oxidation to acetic acid as shown.

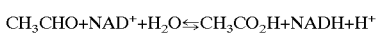

In one embodiment of the invention this can be accomplished by adding acetaldehyde dehydrogenase or an accelerator thereof or a combination of the two. When in vivo, the dehydrogenase should be present in an amount at least chemically equivalent to the amount of blood alcohol or, more precisely, to acetaldehyde, the oxidation product of alcohol. This translates to a concentration in the range 0.1–10 I.U./L.

Optionally the dehydrogenase may be stabilized with zinc ions since the dehydrogenase might otherwise degrade. Preferably, the concentration of zinc ions is at least 1% of the molar concentration of the dehydrogenase.

By increasing the amount of one of the reactants, the equilibrium can be shifted toward product. Thus, a formulation containing $NAD^+$ can be useful. A sufficient quantity of $NAD^+$ is administered to provide an in vivo concentration of $NAD^+$ in the range 0.05% to 5% of the maximum expected in vivo molar concentration of ethanol.

Any combination of the above may also be beneficial. Thus, a formulation containing acetaldehyde dehydrogenase, $NAD^+$, pyridoxamine phosphate and zinc arginate or lysinate (or both) can be useful.

In another embodiment of the invention, the acetaldehyde can be chemically or enzymatically converted to an innocuous derivative, which can later be removed from the body. These derivatives include, but are not limited to, esters, ethers, acetals, ketals and urethanes.

Under proper aerobic conditions and with sufficient acid neutralizing agents, the aerobic oxidation of alcohol to acetic acid catalyzed by Alcohol Oxidase, AO, as shown,

may also be useful, particularly in combination with any of the above schemes.

In another embodiment of the invention, the acetic acid formed in either the acetaldehyde dehydrogenase or the alcohol oxidase reaction, or the combination of the two, can be converted to methane and carbon dioxide through a methanogenetic enzyme, thus driving the alcohol oxidation further toward irreversibility, as shown in equation 4.

In another embodiment of this invention, the enzymatic reaction can be accelerated by a charge-transfer agent such as thiamine, (formula 5), retinoic acid (formula 6), an isoflavonoid or a pyranoside thereof (e.g. daidezin (formula 7) or its 7-glucoside, commonly known as aloin, (formula 8)), and 4,5-Dihydro-4,5-dioxo-1H-pyrrolo[2,3-f]quinoline-2,7,9-tricarboxylic acid, also known as either pyrroloquinolinequinone (PQQ) or methoxatin (formula 9), or any combination thereof. lipoic acid, retinoic acid, retinal, retinol, and derivatives and analogs thereof. A sufficient quantity of the charge-transfer agent is administered to provide an in vivo concentration of the charge-transfer agent in the range from 0.1% and 2% of the maximum expected in vivo molar concentration of ethanol.

In a further embodiment of the invention, various accelerants can be used to supply energy to the forward reactions of equilibria 5 and 6. Such accelerants include adenosine 5'-triphosphate, adenine-9-β-D-arabinofurasnoside 5'-trophosphate, 2'-deoxyadenosine 5'-triphosphate, and 2',3'-dideoxyadenosine 5'-triphosphate. They also include carbohydrates such as fructose, arabinose, ribose, deoxyribose, and their phosphorylated derivatives. A sufficient quantity of the accelerant is administered to provide an in vivo concentration in the range from 1% to 100% of the maximum expected in vivo molar concentration of ethanol.

In another embodiment of this invention, a combination of some or all of the above with substances that prevent or delay the absorption of gastric alcohol into the blood is also envisaged. Such substances include unsaturated fatty acids, dietary fiber, and surfactants such as oleic acid, lecithin, the plant surfactant saponin and taurine (formula 10).

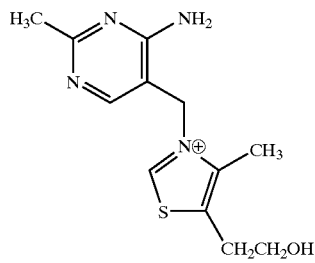

5

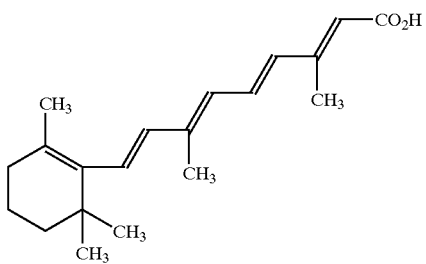

6

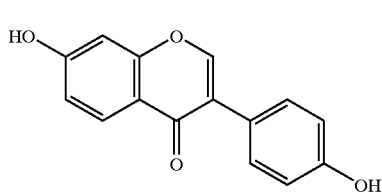

7

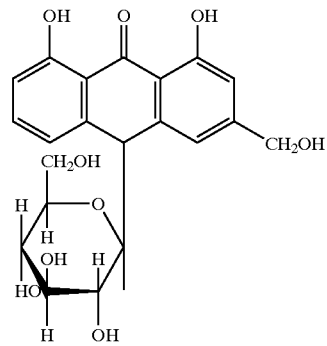

8

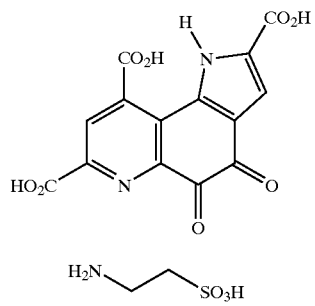

9

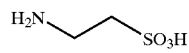

10

The concentration of the surfactant in the composition should be in the range 0.02% and 0.2% by volume.

Some surfactants which also act as charge transfer agents can be used. These include lipoic acid, retinoic acid, retinal, retinol, and derivatives and analogs thereof. The concentration of the combined surfactant and charge-transfer agent should be between 0.1% and 2% of the maximum molar concentration of ethanol. A sufficient quantity of the combined surfactant and charge-transfer agent is administered to provide an in vivo concentration of the surfactant and charge-transfer agent between 0.1% and 2% of the maximum expected molar concentration of ethanol.

In yet another embodiment of this invention, the acceleration is effected by multivalent transition metal ions and their derivatives capable of acting as a pseudo enzyme in a dehydrogenase reaction. The ions include, but are not limited to, ions of elements of Groups IVa through VIII of the Periodic Table and their complexes or any combination thereof.

Preferred sources of such ions include: vanadyl sulfate; potassium ferricyanide; ammonium iron (III) citrate; ammonium molybdate; ammonium phosphomolybdate; sodium tungstate; and sodium phosphotungstate. Other sources include ammonium manganese (III) sulfate; zirconium (IV) EDTA; niobium (IV) EDTA; tetratkis(tropolinato) niobium (V) chloride; tetratkis(tropolinato) tantalum (V) chloride; cobalt (III) hexammine chloride; and chromium (III) picolinate. A sufficient amount of transition metal ion administered to provide an in vivo concentration of the ion in the range 0.05% to 2% of the maximum expected in vivo molar concentration of ethanol.

In the foregoing disclosure some reactions, such as those involving the enzyme ADH, are specific to ethanol, while others may apply also to methanol. In general, the multivalent transition metal ions and their complexes mentioned above would be expected to oxidize methanol and ethanol alike, via reactions which may sometimes involve $NAD^+$. It has been found in particular that vanadyl sulfate/$NAD^+$ is effective in oxidizing methanol. This invention therefore encompasses the in vivo oxidation of both ethanol and methanol in the blood.

Optionally, any of the embodiments can also include dietary constituents such as dietary fiber, garlic oil and onion oil, or medications including such commonly available pain relieving ingredients as aspirin, ibuprofin and acetomenaphin.

EXAMPLES

Examples 1–40 were designed to demonstrate, in a semi-quantitative way the effectiveness of the claimed invention.

In each of the examples, aliquots of reagents were mixed and the final solution allowed to stand for a specified time, after which it was treated with an excess of a reagent containing 2,4-dinitrophenylhydrazine (DNP) in a strongly acidic solution. The reagent quenches any oxidative reaction of alcohol as well as detects the formation of acetaldehyde. An orange, crystalline precipitate indicates a positive reaction. The DNP reagent is a fresh solution of 0.5 gm. of 2.4-dinitrophenylhydrazine in 20 mL methanol and 5 mL concentrated sulfuric acid, diluted to 50 mL of deionized distilled water.

Example 1

To a 0.05M solution of ethanol in a 1M (pH 9.25) phosphate buffer (10 μL) are added 10 μL each of a solution 0.08M in $NAD^+$ (in deionized distilled water) and 4U/mL Alcohol Dehydrogenase (from Equine liver) in the above buffer, and diluted to 100 μL with buffer. At the end of a specified time, it was quenched with the DNP reagent. A positive reaction with DNP was obtained when the alcohol solution was allowed to stand for 2 minutes.

Example 2

The procedure in Example 1 was repeated with the omission of the enzyme solution. The solution tested negative even after being allowed to stand for 15 minutes, indicating that $NAD^+$ cannot oxidize alcohol without a catalyst.

Example 3

The procedure in Example 1 was repeated with the addition of 10 μL of a 0.01M vanadyl sulfate solution in deionized distilled water. The solution tested positive after being allowed to stand for 1 minute, indicating some acceleration.

Example 4

The procedure in Example 3 was repeated with the omission of the enzyme solution. The solution tested positive after being allowed to stand for 2 minutes, indicating that vanadyl sulfate can act as a catalyst or a "pseudo" enzyme for the oxidative reaction.

Example 5

The procedure in Example 4 was repeated with the omission of $NAD^+$. The solution tested negative even after being allowed to stand for 15 minutes, indicating that vanadyl sulfate cannot oxidize alcohol in the absence of $NAD^+$.

Example 6–10

Examples 1–5 were repeated, with almost identical results, using sodium phosphotungstate in place of vanadyl sulfate.

Example 11–15

Examples 1–5 were repeated, with almost identical results, using ammonium molybdate in place of vanadyl sulfate.

Example 16–20

Examples 1–5 were repeated, with almost identical results, using potassium ferricyanide in place of vanadyl sulfate.

Example 21–25

Examples 1–5 were repeated, with almost identical results, using ammonium ferric citrate in place of vanadyl sulfate.

Example 26

The procedure in Example 2 was repeated using a pH 7.25 1M phosphate buffer. The solution tested negative even after being allowed to stand for 15 minutes, indicating that the enzyme is ineffective in vitro at pH 7.25

Example 27

The procedure in Example 2 was repeated using a pH 7.25 1M phosphate buffer. The solution tested negative even after being allowed to stand for 15 minutes, indicating that $NAD^+$ cannot oxidize alcohol without a catalyst.

Example 28

The procedure in Example 3 was repeated using a pH 7.25 1M phosphate buffer. The solution tested positive after being allowed to stand for 2 minutes, indicating that vanadyl sulfate can act as an accelerator for the oxidative reaction, even at the lower pH 7.25.

Example 29

The procedure in Example 4 is repeated using a pH 7.25 1M phosphate buffer. The solution tested positive after being allowed to stand for 2 minutes, indicating that vanadyl sulfate can act as a catalyst or a "pseudo" enzyme for the oxidative reaction, even at the lower pH 7.25.

Example 30

The procedure in Example 5 is repeated using a pH 7.25 1M phosphate buffer. The solution tested negative even after being allowed to stand for 15 minutes, indicating that vanadyl sulfate cannot oxidize alcohol in the absence of $NAD^+$.

Example 31–35

Examples 25–30 were repeated, with almost identical results, using sodium phosphotungstate in place of vanadyl sulfate.

Example 36–40

Examples 25–30 were repeated, with almost identical results, using ammonium ferric citrate in place of vanadyl sulfate.

Examples 41 and 42 were designed to demonstrate together, in a semi-quantitative way, the effectiveness of a particular transition metal (vanadium) compound in catalyzing the oxidation of acetaldehyde to acetic acid.

Example 41

To a 0.0002 M solution of acetaldehyde in deionized distilled water (1 µL) are added 10 µL of a solution 0.0004 M in NAD$^+$ (in deionized distilled water) and 1 U/mL Acetaldehyde Dehydrogenase (from Baker's Yeast) in a 1M (pH 9.25) phosphate buffer (1 µL), and diluted to 100 µL with the above buffer. At the end of a specified time, it was quenched with the DNP reagent. A positive reaction with DNP was obtained when the solution was allowed to stand for 2 minutes; an ambiguous reaction after 5 and 10 minutes, and a negative reaction after 20 minutes. This indicates that the most of the acetaldehyde had been converted.

Example 42

The procedure in Example 41 was repeated replacing the Acetaldehyde Dehydrogenase was replaced by a solution 0.004 M in vanadyl sulfate (in deionized distilled water) (1 µL). An ambiguous reaction was obtained with the DNP reagent after 2 and 5 minutes; a negative reaction was obtained after 10 minutes. This indicates that vanadyl sulfate is at least as effective as Acetaldehyde Dehydrogenase in catalyzing the oxidation of acetaldehyde.

Examples 43–50 were designed to illustrate that various transition metal compounds can effect the oxidation of NADH, thus recycling NAD$^+$, a major feature of any catalyst.

Example 43

A 0.01M solution of NADH in a 1M (pH 9.25) phosphate buffer (10 µL) is diluted to 1900 µL with the buffer and mixed with a 0.01M solution of vanadyl sulfate (10 µL) in a multi-cavity plate. The rate of oxidation of NADH is followed over time as the decrease in the absorption at 340 nm. The results, as summarized in Table 1 and FIG. 1 indicate the effectiveness of vanadyl sulfate and potassium ferricynaide, and to a lesser extent, ammonium molybdate and sodium phosphotungstate, the latter two after an induction period.

Example 44

The procedure in Example 43 is repeated replacing vanadyl sulfate with potassium ferricyanide.

Example 45

The procedure in Example 43 is repeated replacing vanadyl sulfate with sodium molybdate.

Example 46

The procedure in Example 43 is repeated replacing vanadyl sulfate with sodium phosphotungstate.

Examples 47–50

The procedures in Examples 43–46 are repeated using a 1M (pH 7.25) phosphate buffer solution. The results, as summarized in Table 2 and FIG. 2, indicate the effectiveness of vanadyl sulfate and potassium ferricyanide, and to a lesser extent sodium molybdate, the latter after an induction period.

TABLE 1

Kinetics of Transition Metal Oxidation of NADH at pH 9.25

| | Additive | | | | |
|---|---|---|---|---|---|
| | None | Vanadyl Sulfate | Phosphotungstate | Molybdate | Ferricynide |
| Slope (OD/Min) | 0 | .0112 | .007* | .0035* | .0432 |
| Slope (Mole/L/Min) | 0 | .000005 | .0000006 | .0000003 | .00002 |

TABLE 2

Kinetics of Transition Metal Oxidation of NADH at pH 7.25

| | Additive | | | | |
|---|---|---|---|---|---|
| | None | Vanadyl Sulfate | Phosphotungstate | Molybdate | Ferricynide |
| Slope (OD/Min) | 0 | .0079 | 0 | .0025* | .0285 |
| Slope (Mole/L/Min) | 0 | .0000036 | 0 | .00000012 | .000013 |

In Examples 51–53, the rate of ADH catalyzed NAD$^+$ oxidation of alcohol is followed by the rise in absorption at 340 nm, with and without additives. When a solvent (methanol) is needed to dissolve the additive, an equal amount is added to the "blank" or "control". The results, as summarized in Table 3, indicate the effectiveness of Daidezin, Aloin and Methoxatin as accelerators.

Example 51

To a 0.01M solution of ethanol (10 µL) in 1M pH 9.25 phosphate buffer, in a multi-well plate, is added a solution of aloin, of the indicated concentration (10 µL) and 10 µL of a solution containing 0.2 U/mL ADH and diluted to 180 µL with buffer. To the mixture is added 20 µL of a 0.01M solution of NAD$^+$ in deionized distilled water, and the absorbance at 340 mn is followed with time.

Example 52

The procedure in Example 51 is repeated using Daidezin.

Example 53

The procedure in Example 51 is repeated using Methoxatin.

TABLE 3

| Relative rates of Ethanol Oxidation in presence of Additives (Control = 1) | | | | | |
| --- | --- | --- | --- | --- | --- |
| Aloin (.000005 M) | Aloin (.00001 M) | Daidezin (.000005 M) | Daidezin (.00001 M) | Methoxatin (.000005 M) | Methoxatin (.00001 M) |
| 1.07 | 1.19 | 1.28 | 1.38 | 1.29 | 1.59 |

While the invention has been described in connection with various embodiments, it is not intended to limit the scope of the invention to the particular form set forth, but on the contrary, it is intended to cover such alternatives, modifications, and equivalents as may be included within the spirit and scope of the invention as defined by the appended claims.

We claim:

1. A composition for accelerating in vivo oxidation of alcohol, the composition comprising $NAD^+$ and a catalyst comprising at least one of a species selected from the group consisting of a multivalent transition metal ion, and a complex thereof excluding manganese, iron. chromium, copper and zinc; the species being in a state selected to accelerate in vivo oxidation of alcohol in the absence of a dehydrogenase where said catalyst effects the oxidation of NADH, thus recycling $NAD^+$ and the composition having a sufficient quantity of the transition metal ion to provide an in vivo concentration of the ion in the range 0.05% to 2% of a maximum in vivo molar concentration of ethanol.

2. The composition of claim 1 having a quantity of $NAD^+$ sufficient to provide an in vivo concentration of $NAD^+$ in the range 0.05% to 5% of a maximum in vivo molar concentration of ethanol.

3. The composition of claim 1 further comprising a base.

4. The composition of claim 3, having a quantity of the base sufficient to provide an in vivo concentration of the base at least chemically equivalent to an acid resulting from the oxidation of the ethanol.

5. The composition of claim 3 wherein the base is selected from the group consisting of sodium carbonate, sodium bicarbonate, trisodium phosphate, disodium hydrogen phosphate and tris (hydroxymethyl)-aminomethane.

6. The composition of claim 1, having also a medication.

7. The composition of claim 6, the medication being a pain-relief agent selected from the group consisting of aspirin, ibuprofen and acetaminophen.

8. A composition for accelerating in vivo oxidation of alcohol, the composition comprising $NAD^+$ and a catalyst comprising at least one of a species selected from the group consisting of a multivalent transition metal ion, and a complex thereof; the species being in a state selected to accelerate in vivo oxidation of alcohol in the absence of a dehydrogenase where said catalyst effects the oxidation of NADH, thus recycling $NAD^+$; and further comprising an agent reactive with acetaldehyde, the reactive agent being a dehydrogenase.

9. The composition of claim 8, the dehydrogenase being selected from the group consisting of alcohol dehydrogenase and acetaldehyde dehydrogenase.

10. The composition of claim 8 wherein the dehydrogenase has a concentration in the range 0.1 and 10 I. U./L.

11. The composition of claim 8 having a quantity of the reactive agent sufficient to provide an in vivo concentration of the reactive agent at least chemically equivalent to an amount of acetaldehyde resulting from the oxidation of alcohol.

12. The composition of claim 8, further including a stabilizing ion.

13. The composition of claim 12, the stabilizing ion being zinc.

14. The composition of claim 13, the concentration of zinc ions being 1% the molar concentration of the dehydrogenase.

15. A composition for accelerating in vivo oxidation of alcohol, the composition comprising $NAD^+$ and a catalyst comprising at least one of a species selected from the group consisting of a multivalent transition metal ion, and a complex thereof; the species being in a state selected to accelerate in vivo oxidation of alcohol in the absence of a dehydrogenase where said catalyst effects the oxidation of NADH, thus recycling $NAD^+$; and further including an accelerant selected from the group consisting of adenosine 5'-triphosphate, adenine-9-β-D-arabinofurasnoside 5'-triphosphate, 2'-deoxyadenosine 5'-triphosphate, and 2',3'-dideoxyadenosine 5'-triphosphate.

16. The composition of claim 15, having a quantity of the accelerant sufficient to provide an in vivo concentration in the range from 1% to 100% of a maximum in vivo molar concentration of ethanol.

17. A composition for accelerating in vivo oxidation of alcohol, the composition comprising $NAD^+$ and a catalyst comprising at least one of a species selected from the group consisting of a multivalent transition metal ion, and a complex thereof; the species being in a state selected to accelerate in vivo oxidation of alcohol in the absence of a dehydrogenase where said catalyst effects the oxidation of NADH, thus recycling $NAD^+$ and further including a charge-transfer agent selected from the group consisting of an isoflavanone and a pyranoside thereof.

18. The composition of claim 17 wherein the isoflavanoid is daidezin and its pyranoside, aloin.

19. The composition of claim 17 having a quantity of the charge-transfer agent sufficient to provide an in vivo concentration of the charge-transfer agent in the range from 0.1% and 2% of a maximum in vivo molar concentration of ethanol.

20. A composition for accelerating in vivo oxidation of alcohol, the composition comprising NAD$^+$ and a catalyst comprising at least one of a species selected from the group consisting of a multivalent transition metal ion, and a complex thereof; the species being in a state selected to accelerate in vivo oxidation of alcohol in the absence of a dehydrogenase where said catalyst effects the oxidation of NADH, thus recycling NAD$^+$; and further comprising a surfactant.

21. The composition of claim 20, the surfactant being selected from the group consisting of saponin, taurine, oleic acid and lecithin.

22. The composition of claim 20, having a quantity of the surfactant sufficient to provide an in vivo concentration in the range 0.02% and 0.2% by volume.

23. The composition of claim 20, wherein the surfactant is also a charge-transfer agent.

24. The composition of claim 23, wherein the surfactant and charge-transfer agent is selected from the group consisting of lipoic acid, retinoic acid, retinal, retinol, and derivatives and analogs thereof wherein the derivatives and analogs are surfactants that are also charge transfer agents from the group.

25. The composition of claim 23, having a quantity of the surfactant and charge-transfer agent sufficient to provide an in vivo concentration of the surfactant and charge-transfer agent between 0.1% and 2% of a maximum molar concentration of ethanol.

26. A composition for accelerating in vivo oxidation of alcohol, the composition comprising NAD$^+$ and a catalyst comprising at least one of a species selected from the group consisting of a multivalent transition metal ion, and a complex thereof; the species being in a state selected to accelerate in vivo oxidation of alcohol in the absence of a dehydrogenase where said catalyst effects the oxidation of NADH, thus recycling NAD$^+$ and having also a dietary composition selected from the group consisting of garlic oil, onion oil and dietary fiber.

27. A composition for accelerating in vivo oxidation of alcohol, the composition comprising NAD$^+$ and a catalyst comprising at least one of a species selected from the group consisting of a multivalent transition metal ion, a complex thereof; the species being in a state selected to accelerate in vivo oxidation of alcohol in the absence of a dehydrogenase where said catalyst effects the oxidation of NADH, thus recycling NAD$^+$ and the composition being configured in a form selected from the group consisting of a solution, suspension, capsule, gel caplet, transdermal patch, and nasal spray.

28. A composition for accelerating in vivo oxidation of alcohol, the composition comprising NAD$^+$ and one member selected from the group consisting of vanadyl sulfate and a complex of vanadyl sulfate.

29. The composition of claim 28, further comprising a species selected from the group consisting of a multivalent transition metal ion and a complex thereof, the transition metal ion being selected from the group consisting of the elements of Groups IVa through VIII of the Periodic Table.

30. The composition of claim 29, wherein the species is selected from the group consisting of: potassium ferricyanide; ammonium iron (III) citrate; ammonium molybdate; ammonium phospho molybdate; sodium tungstate; sodium phospho tungstate; ammonium manganese (III) sulfate; zirconium (IV) EDTA; niobium (IV) EDTA; tetratkis (tropolinato) niobium (V) chloride; tetratkis(tropolinato) tantalum (V) chloride; cobalt (III) hexamine chloride; and chromium (III) picolinate.

31. The composition of claim 28 having a sufficient quantity of the transition metal ion to provide an in vivo concentration of the ion in the range 0.05% to 2% of a maximum in vivo molar concentration of ethanol.

32. The composition of claim 28 having a quantity of NAD$^+$ sufficient to provide an in vivo concentration of NAD$^+$ in the range 0.05% to 5% of a maximum in vivo molar concentration of ethanol.

33. The composition of claim 28 further comprising a base.

34. The composition of claim 33, having a quantity of the base sufficient to provide an in vivo concentration of the base at least chemically equivalent to an acid resulting from the oxidation of the ethanol.

35. The composition of claim 33 wherein the base is selected from the group consisting of sodium carbonate, sodium bicarbonate, trisodium phosphate, disodium hydrogen phosphate and tris(hydroxymethyl)-aminomethane.

36. The composition of claim 28, further comprising an agent reactive with acetaldehyde.

37. The composition of claim 36, the reactive agent being selected from the group consisting of lysine, arginine, thiamine, and pyridoxamine.

38. The composition of claim 36 having a quantity of the reactive agent sufficient to provide an in vivo concentration of the reactive agent at least chemically equivalent to an amount of acetaldehyde resulting from the oxidation.

39. The composition of claim 36, the reactive agent being a dehydrogenase.

40. The composition of claim 39, the dehydrogenase being selected from the group consisting of alcohol dehydrogenase and acetaldehyde dehydrogenase.

41. The composition of claim 39, wherein the dehydrogenase has a concentration in the range 0.1 and 10 I. U./L.

42. The composition of claim 28, further including an accelerant.

43. The composition of claim 42, the accelerant being selected from the group consisting of adenosine 5'-triphosphate, adenine-9-β-D-arabinofurasnoside 5'-triphosphate, 2'-deoxyadenosine 5'-triphosphate, and 2',3'-dideoxyadenosine 5'-triphosphate.

44. The composition of claim 42, the accelerant being selected from the group consisting of fructose, arabinose, ribose, deoxyribose, and their phosphorylated derivatives.

45. The composition of claim 42, having a quantity of the accelerant sufficient to provide an in vivo concentration in the range from 1% to 100% of a maximum in vivo molar concentration of ethanol.

46. The composition of claim 28, further including a charge-transfer agent.

47. The composition of claim 46, the charge-transfer agent being selected from the group consisting of an isoflavanone and a pyranoside thereof.

48. The composition of claim 47, wherein the isoflavanoid is daidezin and the pyranoside thereof is aloin.

49. The composition of claim 46, the charge-transfer agent being selected from the group consisting of methoxatin, pyridoxine, pyridoxamine, pyridoxamine phosphate and thiamine.

50. The composition of claim 46 having a quantity of the charge-transfer agent sufficient to provide an in vivo concentration of the charge-transfer agent in the range from 0.1% and 2% of a maximum in vivo molar concentration of ethanol.

51. The composition of claim 28, further comprising a surfactant.

52. The composition of claim 51, the surfactant being selected from the group consisting of saponin, taurine, oleic acid and lecithin.

53. The composition of claim 51, the concentration of the surfactant being in the range 0.02% and 0.2% by volume.

54. The composition of claim 51, wherein the surfactant is also a charge-transfer agent.

55. The composition of claim 54, wherein the surfactant and charge-transfer agent is selected from the group consisting of lipoic acid, retinoic acid, retinal, retinol, and derivatives and analogs thereof wherein the derivatives and analogs are surfactants that are also charge transfer agents from the goup.

56. The composition of claim 54, having a quantity of the surfactant and charge-transfer agent sufficient to provide an in vivo concentration of the surfactant and charge-transfer agent between 0.1% and 2% of a maximum molar concentration of ethanol.

57. The composition of claim 39, further including a stabilizing ion.

58. The composition of claim 57, the stabilizing ion being zinc.

59. The composition of claim 58, the concentration of zinc ions being 1% of the molar concentration of a dehydrogenase.

60. The composition of claim 28, further comprising a dietary composition selected from the group consisting of garlic oil, onion oil and dietary fiber.

61. The composition of claim 28, further comprising a medication.

62. The composition of claim 61, the medication being a pain-relief agent selected from the group consisting of aspirin, ibuprofen and acetaminophen.

63. The composition of claim 28, being configured in a form selected from the group consisting of a solution, a suspension, a capsule, a gel caplet, a transdermal patch and a nasal spray.

* * * * *